though this is disclosed nowhere. Following this, the supernatant is removed from the precipitate and the LDL in this supernatant is determined. The determination is carried out by measuring cholesterol or apoprotein B therein.

United States Patent [19]
Kerscher et al.

[11] Patent Number: 4,746,605

[45] Date of Patent: May 24, 1988

[54] PROCESS AND A REAGENT FOR THE DETERMINATION OF LOW DENSITY LIPOPROTEINS (LDL)

[75] Inventors: Lorenz Kerscher, Starnberg; Joachim Ziegenhorn, Starnberg; Sigbert Schiefer, Pahl, all of Fed. Rep. of Germany

[73] Assignee: Boehringer Mannheim GmbH, Mannheim, Fed. Rep. of Germany

[21] Appl. No.: 656,954

[22] Filed: Oct. 2, 1984

[30] Foreign Application Priority Data

Oct. 26, 1983 [DE] Fed. Rep. of Germany ....... 3338836

[51] Int. Cl.$^4$ ............................................. G01N 33/92
[52] U.S. Cl. ......................................... 435/7; 435/11; 435/28; 435/19; 435/26; 436/71; 436/175; 436/536; 436/817; 436/825; 436/826
[58] Field of Search ....................... 424/85; 435/11, 28, 435/19, 26; 436/536, 512, 518, 528, 547, 71, 175, 817, 824, 825, 826, 178

[56] References Cited

U.S. PATENT DOCUMENTS 4,018,662 4/1977 Ruhenstroth-Bauer ............ 436/516
4,211,530 7/1980 Goverde ............................. 436/825
4,399,217 8/1983 Holmquist .......................... 436/71

FOREIGN PATENT DOCUMENTS 3215310 10/1983 Fed. Rep. of Germany ........ 435/11
0103057 6/1982 Japan ................................... 436/71

OTHER PUBLICATIONS

Mangold in Clinical Biochemistry Principals & Methods, vol. II, Walter de Gruyter, N.Y. 1974, pp. 1009–1017.
Kim, J. of Biological Chemistry 254(19), pp. 9621–9629, 1979.

*Primary Examiner*—Robert J. Warden
*Assistant Examiner*—Robert Benson
*Attorney, Agent, or Firm*—Felfe & Lynch

[57] ABSTRACT

A method for determining low density lipoproteins (LDLs) in a body fluid sample, as well as a reagent suited for this use, are taught. The method involves precipitating high density lipoproteins (HDLs) from the sample, using an HDL specific antibody or reactive fragment, and then determining the presence and amount of LDL in the supernatant which results. The reagent contains the HDL specific antibodies, as well as polyanions and divalent cations.

17 Claims, No Drawings

PROCESS AND A REAGENT FOR THE DETERMINATION OF LOW DENSITY LIPOPROTEINS (LDL)

The present invention is concerned with a process and a reagent for the determination of low density lipoproteins (LDL).

The determination of the LDL fraction (low density lipoproteins), also called the $\beta$-lipoprotein fraction, has achieved considerable importance for the differentiated diagnosis of a lipid metabolism disturbance.

Hypercholesterolaemia and hypertriglyceridaemia favour the genesis of atherosclerosis and of heart infarct. Therefore, the determination of cholesterol and triglycerides in serum belong to the most frequently carried out tests in the clinical-chemical routine laboratory.

Numerous investigations of the fat metabolism have come to the conclusion that the individual coronary risk can be better detected when there is determined not only the change of the triglyceride and cholesterol level but also the fundamental pathological shifts in the lipoprotein pattern (Münch. med. Wschr., 121, 1639/1979).

The known plasma lipoproteins contain a differing high proportion of protein (apolipoproteins), phospholipids, cholesterol and triglycerides. On the basis of their behaviour (differing density) in an analytical ultracentrifuge and on the basis of their differing speed of migration in the case of gel electrophoresis, they can be subdivided into four different classes: chylomicrons pre-$\beta$-lipoproteins=VLDL (very low density lipoprotein)

$\beta$-lipoprotein=LDL (low density lipoprotein)

$\alpha$-lipoprotein=HDL (high density lipoprotein)

Investigation of the function of the lipoproteins showed that LDL, within the lipoproteins, represents the decisive atherogenic component, in the case of an increase of which there is present an increased risk of coronary disease. The early recognition and combating of this state is of great importance. Therefore, there is a need for a practical process for the quantitative determination of the LDL concentration in serum and plasma.

Hitherto, for the determination of the LDL cholesterol value, there have essentially been employed four methods which, however, possess disadvantages:

1. Ultracentrifuging.

This process is not a suitable for a routine laboratory since, for this purpose, a special equipment of the apparatus is needed and the carrying out thereof requires an extremely careful working technique and a very high expenditure of time (centrifuging for several days in an ultracentrifuge). Consequently, this analytical process has hitherto been restricted to medical research laboratories.

2. Electrophoretic separation with subsequent visualisation of the lipoprotein bands by polyanion precipitation and conversion of the turbidity units into cholesterol values.

However, this process is time-consuming and necessitates the use of an electrophoresis apparatus, as well as of a densitometer for the evaluation (Lab. Med., 1, 145/1977).

3. Determination of the LDL cholesterol value via the Friedewald formula (Clin. Chem., 18, 499/1972).

For the calculation of the LDL cholesterol value according to the Friedewald formula, the determination of three parameters is necessary: cholesterol, HDL cholesterol and triglyceride value of the sample. Therefore, this method is not sufficiently practicable. Furthermore, this approximation formula only applies for chylomicron-free samples and samples with triglyceride values below 400 mg./dl.

4. Precipitation reactions.

A process in which LDL is precipitated with the help of a lectin is described in published Federal Republic of Germany Patent Application No. 28 57 710. However, in the case of this method, the value for LDL cholesterol can only be determined after redissolving the precipitate or only by differential formation of the cholesterol values before and after precipitation. This represents a considerable disadvantage.

A precipitation method for lipoproteins, in which LDL remains in the supernatant after the precipitation, is described in Federal Republic of Germany Patent Specification No. 26 00 664. However, this method is not sufficiently practicable for use as a routine determination since, for precipitating out the lipoproteins, two working steps are necessary (addition of two differing agents—polyethyleneimine and a cation exchanger—together with an intermediate incubation phase).

Consequently, there is a need for a simple process and reagent with a high degree of practicability and great accuracy for the determination of LDL lipoprotein. According to Federal Republic of Germany Patent Application No. P 32 15 310.4, this problem is solved by a process for the determination of low density lipoproteins (LDL) in body fluids, wherein, to the sample to be investigated, there are added high density lipoprotein (HDL) antibodies, insolubles formed are separated off and the LDL or one of its components is determined in the supernatant.

It has been shown that it would be advantageous if, especially in the case of hyperlipidaemic, i.e. VLDL-rich, sera, the formation of the immune precipitate could be accelerated and the immune complex could be completely centrifuged off even more simply.

Thus, according to the present invention, there is provided a process for the determination of low density lipoproteins (LDL) in body fluids in which high density lipoprotein (HDL) antibodies are added to a sample to be investigated, insolubles formed are separated off and the LDL or one of its components is determined in the supernatant, wherein a mixture of polyanions and divalent cations is added to the antibodies.

The present invention is based upon the surprising ascertainment that, by the addition of a mixture of polyanion and divalent cations, the antibody properties are not disadvantageously influenced. Furthermore, it was hitherto feared that the addition of polyanions would bring about not only the desired precipitating out of VLDL and of other lipoprotein fractions but also the precipitating out of the LDL which it is intended to determine. Surprisingly, however, in the case of salt concentrations which are higher than about 150 mMol/liter, the rapid and complete aggregation of the lipoprotein-antibody complex is favoured by the presence of the polyanions and divalent cations and their centrifugability is increased, without it resulting in a coprecipitation of the LDL. The use of polyanions, such as dextran sulphate, heparin, phosphotungstic acid and polyvinyl sulphate, and of chlorides of divalent cations, such as calcium, magnesium and manganese chloride, has proved to be advantageous. The dextran sulphate can be high molecular (molecular weight of from $5 \times 10^4$ to $2 \times 10^6$) or short-chained (molecular weight of from 5000 to 50,000). It can be especially advantageous to bind the antibodies covalently to dextran sulphate or heparin, the bonding thereby taking place according to conventional methods and the conjugates thus obtained being used in the test together with calcium, magnesium or manganese chloride.

The preferred concentration ranges of the polyanions in the reaction mixture are 0.1 to 8 g./liter in the case of high molecular weight dextran sulphate, from 1 to 15 g./liter in the case of short-chained dextran sulphate and heparin, from 0.2 to 5 g./liter in the case of polyvinyl sulphate and from 0.3 to 6 g./liter in the case of phosphotungstic acid. The concentration of the divalent metal ions to be added is preferably from 10 to 250 mMole/liter in the reaction mixture. Furthermore, the reaction mixture preferably contains sodium chloride in a concentration of from 0.1 to 1 mole/liter. The buffer to be used can be a conventional buffer solution buffering in a pH range of about 6.5 to 8.5, such as MES (morpholino-ethane-sulphonic acid), triethanolamine, MOPS (morpholino-propane-sulphonic acid) or tris buffer. The antibodies are preferably present in a concentration corresponding to 1 to 100 g./l. of $\gamma$-globulin.

The LDL fraction remaining in the supernatant of the reagent can then be determined according to the methods usual for this purpose. The determination of the bound cholesterol present therein preferably takes place with the use of the methods known for this purpose. Thus, the determination can, for example, take place by saponification with alcoholic potassium hydroxide solution and chemical determination according to Liebermann-Burchard. However, it is preferred to use an enzymatic determination with the use of cholesterol oxidase and of a cholesterol ester-splitting enzyme or enzyme system, such as especially cholesterol esterase. In the case of the use of the latter method, there can be determined the amount of oxygen consumed, the amount of cholestenone formed or, most preferably, the amount of hydrogen peroxide formed, using the methods known for this purpose. Since the determination of the bound cholesterol is well known, it is here not necessary to describe it in detail. However, it is to be noted that, in the scope of the present invention, by means of the removal of the VLDL and chylomicron fractions, the appearance of turbidities is prevented, which could disturb an optical measurement of cholestenone or of hydrogen peroxide in the scope of colour reactions. Therefore, the process is suitable to an especial degree in combination with a colorimetrical cholesterol determination method.

However, instead of the cholesterol contained in the LDL fraction or of other LDL components, such as apolipoprotein B, phospholipids and triglycerides, it is also possible to determine the LDL fraction itself, in which case known methods can also be employed. By way of example, there may be mentioned the nephelometric determination or the turbidimetric determination described in published Federal Republic of Germany Patent Application No. 30 07 764.

In the scope of the present invention, the HDL antibodies are preferably employed either in the form of a defatted HDL antiserum or in the form of HDL antibody fractions purified therefrom. It is also possible to use HDL antibody fragments, for example Fab, $Fab_2$ and Fab' fragments. It is equally possible to use antibodies against the apolipoproteins A, C and/or E of the HDL or fragments thereof. Finally, there can also be used monoclonal HDL antibodies.

The preparation of the antibodies used according to the present invention takes place with the use of pure HDL or of one of the mentioned apolipoproteins as immunogen. The antisera thus obtained can be delipidised by treatment with "Aerosil" (Registered Trade Mark). The $\gamma$-globulin fraction is possibly subsequently isolated by ammonium sulphate fractionation.

For obtaining the antibodies, there can be used the animal species usually employed for this purpose, sheep and rabbits being preferred. For obtaining the antibodies, apart from the already-mentioned animals or comparable animals, there can also be used cell cultures.

The separation of the immune aggregate formed in the case of the addition of the HDL antibodies can also take place according to conventional methods. If soluble HDL antibodies are used, then separation preferably takes place by centrifuging. If immobilised, carrier-bound HDL antibodies are used, then the immune aggregate can be separated by simple separation of the liquid phase from the compact solid phase, for example with a solid body coated with antibodies. If antibodies are used obtained with the use of apolipoproteins as immunogens, then preferably those are employed in which the apolipoprotein used as immunogen has a lipid envelope. This can, for example, be achieved in that, after the conventional delipidisation and subsequent fractionation of the apolipoproteins, the selected apolipoprotein A, C and/or E fraction is again relipidated. However, as immunogen there is preferably used purified complete HDL fraction. The purification advantageously takes place in known manner by isolation in an ultracentrifuge. In addition, there can possibly be carried out a further purification via, for example, immobilised concanavalin A or according to the methods of affinity chromatography or of electrophoresis. These methods are well known and do not need to be described here in detail.

The present invention also provides a reagent for the determination of the LDL fraction in body fluids which contains HDL antibodies and a mixture of polyanions and divalent cations.

In a preferred embodiment, the reagent according to the present invention contains, in addition to the already mentioned HDL antibodies or the fragments or antibodies or fragments of HDL components described above in detail in the case of the explanation of the process, also a reagent for the determination of cholesterol.

A preferred reagent of the above-mentioned kind contains cholesterol oxidase, a cholesterol ester-splitting enzyme or enzyme system, a system for the determination of hydrogen peroxide and a surface-active agent.

According to an especially preferred embodiment of the above-mentioned reagent, this consists essentially of HDL antibodies, cholesterol oxidase, cholesterol esterase, peroxidase, 3,4-dichlorophenol, phenol, 4-aminophenazone, a non-ionic detergent, magnesium aspartate and a buffer (pH 7 to 8.5).

The reagent according to the present invention preferably contains the antibodies in a concentration range of from $10^{-7}$ to $10^{-3}$ mole/liter (or kilo of solid body), corresponding to 0.015 to 150 g/l of IgG, referred to the determination solution. The antibody can be present in solid form, preferably lyophilised, or in the form of a solution. As solvent there can be used serum medium, buffer, for example 0.01 to 0.5M tris buffer (pH 7 to 8.5) or 0.01 to 0.5M morpholinopropanesulphonic acid (pH 6.5 to 7.5), in each case with the addition of 0.15 to 1M sodium chloride. If the antibody is used in immobilised form, examples of appropriate carrier substances include polysaccharides, such as cellulose, dextran, starch and derivatives thereof, silicates, polyamides, collagen, latex, aluminium oxide, bovine serum albumin and similar carrier substances. The antibody can also be present bound to the surface of test containers, such as synthetic resin reagent vessels.

An important advantage of the process according to the present invention is that fact that, after the addition of a single reagent, the lipoprotein classes—with the exception of LDL—can be removed from the sample and the diagnostically important LDL content or the cholesterol content of the LDL fraction is subsequently accessible to a direct measurement without further sample pretreatment. Furthermore, it is advantageous that the triglyceride-rich lipoprotein classes in the sample giving rise to turbidities are removed so that, for the subsequent LDL or cholesterol determination, a clear sample is available.

The following Examples are given for the purpose of illustrating the present invention:

EXAMPLE 1

(A) Preparation of purified HDL.

After separation of VLDL and LDL in an ultracentrifuge, in an ultracentrifuge there was isolated a narrow HDL fraction (d 1.080 to 1.210), for example in the manner described by V. P. Skipski, Lipid composition of lipoproteins in normal and diseased states, in Blood Lipids and Lipoproteins: Quantitation, Composition and Metabolism, pub. Nelson, Wiley, New York, 1972, pp 471–583. The fraction was subsequently sedimented or floated twice at the densities of 1.080 and 1.210.

The HDL fraction was purified by affinity chromatography via immobilised concanavalin A (Febs Lett., 91, 174–198/1974) or electrophoretically by means of geonpevision block electrophoresis according to R. W. Mahley, K. S. Holcombe, J. Lipid Res., 18, 314–324/1977).

(B) Preparation of the antiserum.

Animal species: sheep or rabbit

With the use of immunogen obtained according to (A), there was employed the following immunisation scheme:

| day | administration | amount of immunogen |
|---|---|---|
| 0 | intradermally | 1 mg. of protein (HDL) emulsified in Freund's adjuvant |
| 7 | intramuscularly | 1 mg. of protein (HDL) emulsified in Freund's adjuvant |
| 14 | subcutaneously | 1 mg. of protein (HDL) emulsified in Freund's adjuvant |
| 30 | intramuscularly | 1 mg. of protein (HDL) emulsified in Freund's adjuvant |
| 60 | subcutaneously | 1 mg. of protein (HDL) emulsified in Freund's adjuvant |
| every further 30 days | subcutaneously | 1 mg. of protein (HDL) emulsified in Freund's adjuvant |

The first blood sampling was taken after 45 days.

(C) Preparation of anti-HDL-$\gamma$-globulin (delipidated).

1 Liter of crude serum was stirred at ambient temperature with 15 g. "Aerosil" 380 (Degussa) for 1 hour and subsequently centrifuged at 5000 g for 20 minutes. The supernatant was mixed with ammonium sulphate up to an end concentration of 1.7 mole/liter and stirred for 2 hours. After centrifuging at 20,000 g for 30 minutes, the precipitate was dissolved in 200 ml. phosphate-buffered (pH 7.4) physiological sodium chloride solution and completely separated from ammonium sulphate by dialysis. The so obtained $\gamma$-globulin fraction was freed from insoluble protein by centrifuging for 2 hours at 50,000 g.

EXAMPLE 2

30 $\mu$l. of serum sample were added to 0.4 ml. of a mixture of 1 g./liter dextran sulphate (average molecular weight 500,000), 0.3 mole/liter sodium chloride, 50 mMole/liter calcium chloride and 15 mg. anti-HDL-$\gamma$-globulin (delipidated), which had been obtained as described in Example 1, in 0.1 mole/liter tris/HCl buffer (pH value 8.0). After incubating for 30 minutes at ambient temperature, centrifuging was carried out for 2 minutes at 10,000 g. Corresponding control experiments were carried out in parallel under corresponding conditions but with the omission of dextran sulphate and calcium chloride.

300 $\mu$l. of the clear precipitation supernatant were mixed with 2 ml. of a reagent which contained 0.1 mole/liter tris buffer (pH 7.7), 0.05 mole/liter magnesium aspartate, 1 mMole/liter 4-aminophenazone, 6 mMole/liter phenol, 4 mMole/liter 3,4-dichlorophenol, 0.3% fatty alcohol polyglycol ether, 400 U/liter cholesterol esterase, 250 U/liter cholesterol oxidase and 200 U/liter peroxidase.

After incubation for 20 minutes at ambient temperature, the extinction of the sample was measured against the reagent blank (the reagent blank contained 50 l. of the antiserum and took into account the cholesterol content of the antiserum).

$$\Delta E = \Delta E_{sample} - \Delta E_{reagent\ blank}$$

$$\text{LDL cholesterol (mg./dl.)} = 894 \times \Delta E$$

The results obtained are set out in the following Table:

| serum | total triglycerides (mg/dl) | reference method NIH process* | | immune precip. incl. dextran sulph + Ca$^{2+}$ | | immune precip. without dextran sulph + Ca$^{2+}$ | |
|---|---|---|---|---|---|---|---|
| | | LDL-Chol. (mg/dl) | LDL-TG (mg/dl) | LDL-Chol. (mg/dl) | LDL-TG (mg/dl) | LDL-Chol. (mg/dl) | LDL-TG (mg/dl) |
| 1 | 1049 | 89 | 52 | 91 | 78 | 154 | 471 |
| 2 | 333 | 143 | 69 | 128 | 83 | 158 | 175 |

-continued

| serum | total triglycerides (mg/dl) | reference method NIH process* | | immune precip. incl. dextran sulph + Ca²⁺ | | immune precip. without dextran sulph + Ca²⁺ | |
|---|---|---|---|---|---|---|---|
| | | LDL-Chol. (mg/dl) | LDL-TG (mg/dl) | LDL-Chol. (mg/dl) | LDL-TG (mg/dl) | LDL-Chol. (mg/dl) | LDL-TG (mg/dl) |
| 3 | 227 | 137 | 61 | 134 | 56 | 141 | 126 |
| 4 | 806 | 156 | 46 | 141 | 52 | 187 | 388 |
| 5 | 231 | 133 | 44 | 129 | 49 | 135 | 114 |
| 6 | 218 | 158 | 64 | 159 | 72 | 198 | 146 |

TG = triglycerides
*The NIH process was used as reference method: after separation of the VLDL and chylomicrons in an ultracentrifuge, LDL was precipitated. From the difference of the cholesterol values before and after precipitation, there was obtained the value for LDL cholesterol (see Manual of Laboratory Operations, Lipid Research Clinics Program, Lipid and Lipoprotein Analysis, DHEW Publication No. 65-628.

Comparable results were obtained with 1 g./liter of dextran sulphate (molecular weight 2,000,000). Instead of calcium ions, there could also be used magnesium ions or manganese ions in the same concentration. The following concentration ranges are preferred: high molecular weight dextran sulphate 0.1 to 8 g./liter, divalent cation 10 to 250 mMole/liter, sodium chloride 0.2 to 1 mole/liter.

EXAMPLE 3

30 μl. of serum sample were added to 0.4 ml. of a mixture of 5 g./liter short-chained dextran sulphate (average molecular weight 5000), 0.25 mole/liter sodium chloride, 0.15 mole/liter calcium chloride and 15 mg. anti-HDL-γ-globulin (delipidated) in 0.1 mole/liter tris/HCl buffer (pH 8.0). After incubation for 30 minutes at ambient temperature, centrifuging was carried out at 10,000 g. for 2 minutes and the cholesterol, as well as triglycerides, were measured in the supernatant by the method described in Example 1(C). Corresponding control experiments were carried out in parallel under corresponding conditions but with the omission of dextran sulphate and calcium ions. The results obtained are set out in the following Table:

| serum | total triglycerides (mg/dl) | reference method NIH process | | immune precip. incl. dextran sulph + Ca²⁺ | | immune precip. without dextran sulph + Ca²⁺ | |
|---|---|---|---|---|---|---|---|
| | | LDL-Chol. (mg/dl) | LDL-TG (mg/dl) | LDL-Chol. (mg/dl) | LDL-TG (mg/dl) | LDL-Chol. (mg/dl) | LDL-TG (mg/dl) |
| 1 | 329 | 158 | 54 | 154 | 68 | 170 | 210 |
| 2 | 344 | 314 | 89 | 301 | 104 | 362 | 209 |
| 3 | 512 | 246 | 79 | 236 | 85 | 265 | 268 |
| 4 | 736 | 171 | 80 | 174 | 65 | 241 | 312 |
| 5 | 197 | 135 | 102 | 137 | 85 | 134 | 119 |
| 6 | 668 | 157 | 75 | 142 | 89 | 199 | 343 |

Comparable results were obtained with 0.5 g./liter dextran sulphate (molecular weight 15,000), 0.8 g./liter heparin or 0.2 g./liter polyvinyl sulphate. Instead of calcium ions, there could also be used magnesium ions or manganese ions in corresponding concentration. Advantageous concentration ranges are short-chained dextran sulphate or heparin 1 to 15 g./liter, polyvinyl sulphate 0.2 to 5 g./liter, divalent cation 20 to 250 mMole/liter and sodium chloride 0.15 to 0.8 mole/liter.

EXAMPLE 4

30 μl. of serum sample were added to 0.4 ml. of a mixture of 1.15 g./liter phosphotungstic acid, 20 mMole/liter magnesium chloride, 0.3 mole/liter sodium chloride and 15 mg. anti-HDL-γ-globulin (delipidated). After incubation for 30 minutes at ambient temperature, centrifuging at 10,000 g was carried out for 2 minutes and cholesterol as well as triglycerides were measured in the supernatant. Control experiments were carried out in parallel but with the omission of dextran sulphate and calcium chloride. The results obtained are set out in the following Table:

| Serum | total triglyceride | reference method NIH process | | immune precip. incl. PVS/Mg²⁺ | | Immune precip. without addition | |
|---|---|---|---|---|---|---|---|
| | | LDL-Chol. (mg/dl) | LDL-TG (mg/dl) | LDL-Chol. (mg/dl) | LDL-TG (mg/dl) | LDL-Chol. (mg/dl) | LDL-TG (mg/dl) |
| 1 | 329 | 158 | 54 | 150 | 57 | 170 | 270 |
| 2 | 344 | 314 | 89 | 299 | 99 | 362 | 209 |
| 3 | 512 | 246 | 79 | 241 | 83 | 265 | 268 |
| 4 | 736 | 171 | 80 | 164 | 72 | 249 | 312 |
| 5 | 147 | 135 | 102 | 131 | 83 | 134 | 119 |
| 6 | 668 | 157 | 75 | 153 | 78 | 199 | 343 |

PVS = polyvinyl sulphate

The advantageous concentration ranges are 0.3 to 6 g./liter phosphotungstic acid and 10 to 200 mMole/liter magnesium ions.

It will be understood that the specification and examples are illustrative but not limitative of the present invention and that other embodiments within the spirit and scope of the invention will suggest themselves to those skilled in the art.

What is claimed is:

1. A process for the determination of low density lipoprotein (LDL) in a body fluid sample comprising adding an amount of high density lipoprotein (HDL) specific antibodies or reactive fragments thereof sufficient to precipitate said HDL completely and a mixture of polyanion and divalent cation sufficient to precipitate very low density lipoprotein (VLDL) and to enhance precipitation of the antibody-HDL complex without precipitation of LDL to the body fluid sample, wherein said polyanion is dextran sulphate, heparin, phosphotungstic acid or polyvinyl sulphate and said divalent cation is a calcium, magnesium or manganese ion, thereafter separating off the supernatant which is formed and determining the LDL or one of its components in the supernatant.

2. The process of claim 1 wherein the reaction mixture comprises 0.1 to 15 g/liter polyanions and 10 to 250 mMole/liter divalent cations.

3. The process of claim 1 wherein the reaction mixture comprises high molecular weight dextran sulphate in a concentration of from 0.1 to 8 g./liter, short-chained dextran sulphate in a concentration of from 1 to 15 g./liter, heparin in a concentration of from 1 to 15 g./liter, polyvinyl sulphate in a concentration of from 0.2 to 5 g./liter, phosphotungstic or acid in a concentration of from 0.3 to $\neq$g./liter, and divalent cations in a concentration of from 10 to 250 mMole/liter.

4. The process of claim 1 wherein the reaction mixture comprises 0.1 to 15 g./liter polyanions and 10 to 250 mMole/liter divalent cation.

5. The process of claim 1 wherein the LDL is cholesterol.

6. The process of claim 1 wherein the antibody is present in the form of defatted antiserum or as a purified antibody fraction.

7. The process of claim 1 wherein fragments of HDL antibodies are used.

8. The process of claim 6, further comprising raising the antibodies with purified HDL or apolipoprotein A, C and/or E as immunogen.

9. The process of claim 1 wherein antibodies raised in sheep or rabbits are used.

10. The process of claim 1 wherein the antibody is covalently bound to the polyanion.

11. A reagent for the determination of the LDL fraction in a body fluid sample comprising an amount of HDL specific antibodies or reactive fragments thereof sufficient to precipitate HDL completely and a mixture of polyanion and divalent cation sufficient to precipitate VLDL and to enhance precipitation of the antibody-HDL complex without precipitation of LDL, wherein said polyanion is dextran sulphate, heparin, phosphotungstic acid or polyvinyl sulphate and said divalent cation is a calcium, magnesium, or manganese ion.

12. The reagent of claim 11 comprising the HDL antibodies in a concentration corresponding to 1 to 100 g./l. of gamma-globulin; the polyanions in a concentration of from 0.1 to 15 g./liter and the divalent cations in a concentration of from 10 to 250 mMole/liter.

13. The reagent of claim 11 further comprising a reagent for the determination of cholesterol.

14. The reagent of claim 3 wherein the reagent for the determination of cholesterol contains cholesterol oxidase, a cholesterol ester-splitting enzyme or enzyme system, a system for the determination of hydrogen peroxide and a surface-active agent.

15. The reagent of claim 13, wherein the reagent for determination of cholesterol contains HDL antibodies, cholesterol oxidase, cholesterol esterase, peroxidase, 3,4-dichlorophenol, phenol, 4-aminophenazone, a nonionic detergent, magnesium aspartate and buffer (pH 7 to 8.5).

16. The reagent of claim 11 wherein the HDL antibodies are in immobilised form.

17. The reagent of claim 11 wherein the HDL antibodies are covalently linked with the polyanion.

* * * * *

UNITED STATES PATENT AND TRADEMARK OFFICE
CERTIFICATE OF CORRECTION

PATENT NO. : 4,746,605

DATED : May 24, 1988

INVENTOR(S) : Lorenz Kerscher, et al.

It is certified that error appears in the above-identified patent and that said Letters Patent is hereby corrected as shown below:

Claim 3, line 7: change "phosphotungstic or" to -- or phosphotunsgstic --.

Claim 3, line 8: change "≠" to -- 6 --.

Claim 14, line 1: change "3" to -- 13 --.

Signed and Sealed this

Fourteenth Day of March, 1989

Attest:

DONALD J. QUIGG

Attesting Officer

Commissioner of Patents and Trademarks